(12) United States Patent
Verma et al.

(10) Patent No.: US 11,147,524 B2
(45) Date of Patent: *Oct. 19, 2021

(54) WEARABLE MEDICAL DETECTOR

(71) Applicant: Biogen MA Inc., Cambridge, MA (US)

(72) Inventors: Ajay Verma, Needham, MA (US); Marisa J. Bober, Everett, MA (US); Victoria Cabot, Somerville, MA (US); Courtney D. Hilliard, Cambridge, MA (US); Ara N. Knaian, Newton, MA (US); Seth O. Newburg, Arlington, MA (US); John William Hoppin, Boston, MA (US); Karl F. Schmidt, Watertown, MA (US)

(73) Assignee: Biogen MA Inc., Cambridge, MA (US)

( * ) Notice: Subject to any disclaimer, the term of this patent is extended or adjusted under 35 U.S.C. 154(b) by 93 days.

This patent is subject to a terminal disclaimer.

(21) Appl. No.: 16/229,671

(22) Filed: Dec. 21, 2018

(65) Prior Publication Data

US 2019/0200943 A1 Jul. 4, 2019

Related U.S. Application Data

(63) Continuation of application No. 15/275,154, filed on Sep. 23, 2016, now Pat. No. 10,206,639.

(Continued)

(51) Int. Cl.
*A61B 5/0275* (2006.01)
*A61B 6/00* (2006.01)
(Continued)

(52) U.S. Cl.
CPC .......... *A61B 6/4405* (2013.01); *A61B 5/0024* (2013.01); *A61B 5/0275* (2013.01);
(Continued)

(58) Field of Classification Search
None
See application file for complete search history.

(56) References Cited

U.S. PATENT DOCUMENTS

| 4,633,881 A | 6/1987 | Moore et al. |
| 4,682,604 A | 7/1987 | Fymat et al. |

(Continued)

FOREIGN PATENT DOCUMENTS

| DE | 2641039 A1 | 3/1978 |
| DE | 19607157 A1 | 2/1997 |

(Continued)

OTHER PUBLICATIONS

U.S. Appl. No. 16/462,518, filed May 20, 2019, Verma et al.

(Continued)

*Primary Examiner* — Brian T Gedeon
(74) *Attorney, Agent, or Firm* — Wolf, Greenfield & Sacks, P.C.

(57) ABSTRACT

Various embodiments of medical detector systems as well as their methods of operation are disclosed. In one embodiment, one or more detectors are coupled to wearable structures for detecting at least a first tracer within a body portion. In another embodiment, one or more detectors are coupled to a wearable structure, where the detector corresponds to a CMOS chip that directly detects a first radioactive tracer.

20 Claims, 11 Drawing Sheets

Related U.S. Application Data

(60) Provisional application No. 62/232,873, filed on Sep. 25, 2015.

(51) Int. Cl.
    *A61B 5/00*           (2006.01)
    *A61B 6/03*           (2006.01)
    *A61B 6/04*           (2006.01)

(52) U.S. Cl.
    CPC .......... *A61B 5/6803* (2013.01); *A61B 5/6805* (2013.01); *A61B 6/037* (2013.01); *A61B 6/04* (2013.01); *A61B 6/4258* (2013.01); *A61B 6/4266* (2013.01); *A61B 6/4275* (2013.01); *A61B 6/4429* (2013.01); *A61B 6/481* (2013.01); *A61B 6/501* (2013.01); *A61B 6/506* (2013.01)

(56) References Cited

U.S. PATENT DOCUMENTS

| | | | |
|---|---|---|---|
| 5,007,427 | A | 4/1991 | Suzuki et al. |
| 5,111,818 | A | 5/1992 | Suzuki et al. |
| 5,583,343 | A | 12/1996 | Dilmanian et al. |
| 5,647,363 | A | 7/1997 | Rabito et al. |
| D400,196 | S | 10/1998 | Cameron et al. |
| 5,967,983 | A | 10/1999 | Ashburn |
| 6,242,743 | B1 | 6/2001 | DeVito et al. |
| 6,429,431 | B1 | 8/2002 | Wilk |
| 6,574,513 | B1 | 6/2003 | Collura et al. |
| 6,583,420 | B1 | 6/2003 | Nelson et al. |
| 6,690,397 | B1 | 2/2004 | Daignault, Jr. |
| 7,015,460 | B2 | 3/2006 | Nelson et al. |
| D533,875 | S | 12/2006 | Miles et al. |
| 7,391,028 | B1 | 6/2008 | Rubenstein |
| 7,500,746 | B1 | 3/2009 | Howell et al. |
| 7,541,599 | B2 | 6/2009 | Moritake et al. |
| D614,634 | S | 4/2010 | Nilsen |
| 7,737,410 | B2 | 6/2010 | Rubenstein |
| D619,609 | S | 7/2010 | Meziere |
| 7,884,331 | B2 | 2/2011 | Majewski et al. |
| 8,158,950 | B2 | 4/2012 | Rubenstein |
| 8,324,589 | B2 | 12/2012 | Rubenstein |
| D690,716 | S | 10/2013 | Thomsen et al. |
| 9,044,150 | B2 | 6/2015 | Brumback et al. |
| 9,110,115 | B2 | 8/2015 | Marashdeh et al. |
| D739,438 | S | 9/2015 | Torres et al. |
| 9,180,302 | B2 | 11/2015 | Drees et al. |
| 9,226,717 | B2 | 1/2016 | Tashima et al. |
| D752,646 | S | 3/2016 | Miles et al. |
| D795,890 | S | 8/2017 | Verma et al. |
| 9,924,913 | B2 | 3/2018 | Majewski et al. |
| 9,943,278 | B2 | 4/2018 | Nagler et al. |
| 10,206,639 | B2 | 2/2019 | Verma et al. |
| 2004/0259270 | A1 | 12/2004 | Wolf |
| 2006/0262461 | A1* | 11/2006 | Wood ................ H01L 27/14634 361/1 |
| 2009/0299210 | A1 | 12/2009 | Marcarian |
| 2010/0100848 | A1 | 4/2010 | Ananian et al. |
| 2011/0054577 | A1 | 3/2011 | Latham |
| 2012/0290051 | A1* | 11/2012 | Boyden ................ A61N 1/3605 607/113 |
| 2013/0071826 | A1 | 3/2013 | Johnson |
| 2014/0012108 | A1 | 1/2014 | McPeak |
| 2014/0321723 | A1 | 10/2014 | Orcutt et al. |
| 2014/0378794 | A1 | 12/2014 | Conrad et al. |
| 2015/0182121 | A1 | 7/2015 | Barbour et al. |
| 2015/0213214 | A1 | 7/2015 | Patak et al. |
| 2015/0297160 | A1 | 10/2015 | Orcutt et al. |
| 2015/0346353 | A1 | 12/2015 | Gray |
| 2016/0008204 | A1 | 1/2016 | Elliot |
| 2016/0029983 | A1 | 2/2016 | Verma et al. |
| 2016/0058644 | A1 | 3/2016 | Cheathan, III et al. |
| 2017/0086763 | A1 | 3/2017 | Verma et al. |
| 2019/0320989 | A1 | 10/2019 | Verma et al. |

FOREIGN PATENT DOCUMENTS

| | | |
|---|---|---|
| DE | 10261342 A1 | 7/2004 |
| WO | WO 2010/033159 A1 | 3/2010 |
| WO | WO 2010/038176 A1 | 4/2010 |
| WO | WO 2014/114555 A1 | 7/2014 |

OTHER PUBLICATIONS

International Search Report and Written Opinion for International Application No. PCT/US2016/053428, dated Mar. 7, 2017.
[No Author Listed] Portable PET Helmet Captures Images of the Human Brain in Motion. Mary Babb Randolph Cancer Center. http://www.pethelmet.org/single-post/2015/06/10/Portable-PET-helmet-captures-images-of-the-human-brain-in-motion [dated Jun. 9, 2015; last accessed Jan. 12, 2017].
Bojsen et al., Portable cadmium telluride detectors and their applicability for external measurement of 51Cr-EDTA clearance. Int J Appl Radiat Isot. Oct. 1981;32(10):719-27.
Ishaque, Imaging the Brain in Real-Time with a PET-Enabled "Helmet-Cam". http://www.geglobalresearch.com/blog/imaging-brain-real-time-pet-enabled-helmet-cam [dated Sep. 30, 2014; last accessed Dec. 15, 2016] 5 pages.
Lewis, Wearable Brain Scanner Measures Activity on the Go. http://www.pethelmet.org/single-post/2015/01/23/Wearable-Brain-Scanner-Measures-Activity-on-the-Go [dated Jan. 23, 2015; last accessed Jan. 12, 2017].
Prout et al., Detector concept for OPET, a combined PET and optical imaging system. IEEE. 2003;4:2252-6.
U.S. Appl. No. 14/774,577, filed Sep. 10, 2015, Verma et al.
PCT/US2016/053428, Mar. 7, 2017, International Search Report and Written Opinion.
Virtanen et al., Functional brown adipose tissue in healthy adults. New England Journal of Medicine. Apr. 9, 2009;360(15):1518-25.

* cited by examiner

WEARABLE MEDICAL DETECTOR

RELATED APPLICATIONS

This application is a continuation of U.S. application Ser. No. 15/275,154 filed on Sep. 23, 2016, which claims the benefit of priority under 35 U.S.C. § 119(e) of U.S. Provisional Application Ser. No. 62/232,873 filed on Sep. 25, 2015, the contents of each of which are incorporated herein by reference in their entirety.

FIELD

Disclosed embodiments are related to wearable medical detectors.

BACKGROUND

Medical imaging techniques that rely on detection of emissions from tracers originating from within the body of a subject are widely used for diagnosis of various diseases and other medically relevant applications. Nuclear physics-based molecular imaging techniques, such as positron emission tomography (PET) and single photon emission computed tomography (SPECT) allow imaging of subjects using radioactive isotopes. For example, SPECT is based on the use of radioisotopes that emit gamma rays and PET is based on the use of radioisotopes that emit positrons, which annihilate electrons to produce gamma rays. In contrast to nuclear imaging techniques, fluorescence based optical imaging techniques do not involve ionizing radiation such as gamma rays. Instead, fluorescence imaging relies on the excitation of fluorescent tracers by an excitation source that results in the absorption of photons by the fluorophores, and the subsequent detection of photons emitted by the fluorescent tracers as they decay from their excited state. A disadvantage of the various imaging techniques that rely on internal tracers, such as PET, SPECT and fluorescence imaging, is that they rely on the use of large scale and expensive scanners for the detection of emissions from these internal tracers, thereby requiring costly visits to radiology clinics.

SUMMARY

In one embodiment, a medical detector system includes at least a first wearable structure and one or more first detectors that are coupled to the at least first wearable structure such that the one or more first detectors are positioned proximate to a head of a subject when the at least first wearable structure is worn by the subject. The one or more first detectors detect at least a first tracer within a brain of the subject. The medical detector system may also include one or more second detectors that are coupled to the at least first wearable structure such that the one or more second detectors are positioned proximate to a spine of the subject when the at least first wearable structure is worn by the subject. The one or more second detectors detect the at least first tracer within the spine of the subject.

In another embodiment, a medical detector system includes a wearable structure and at least three detectors coupled to the wearable structure such that the at least three detectors are positioned proximate to a spine of a subject when the wearable structure is worn by the subject. The at least three detectors are distributed along a length of the spine from and/or between a lumbar cistern and a cisterna magna of the subject, and the at least three detectors detect at least a first tracer within the spine of the subject.

In yet another embodiment, a medical detector system includes a wearable structure for wearing on a subject's torso and a plurality of detectors coupled to the wearable structure such that the plurality of detectors extend along a spine of the subject when the wearable structure is worn by the subject. The plurality of detectors detect at least a first tracer within the spine of the subject. The medical detector system also includes one or more adjustment devices that maintain the plurality of detectors proximate to the spine of the subject when the wearable structure is worn by the subject.

In another embodiment, a medical detector system includes a wearable structure and a first detector coupled to the wearable structure such that the first detector is positioned proximate to a body portion of a subject when the wearable structure is worn by the subject. The first detector includes a CMOS chip that directly senses the presence of at least a first radioactive tracer within the body portion of the subject.

In yet another embodiment, a medical detector system includes a structure sized and shaped to be positioned and held within a mouth of a subject and a first detector coupled to the structure. The first detector detects at least a first tracer present within the brain of the subject when the structure is located in the mouth of the subject.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1A:
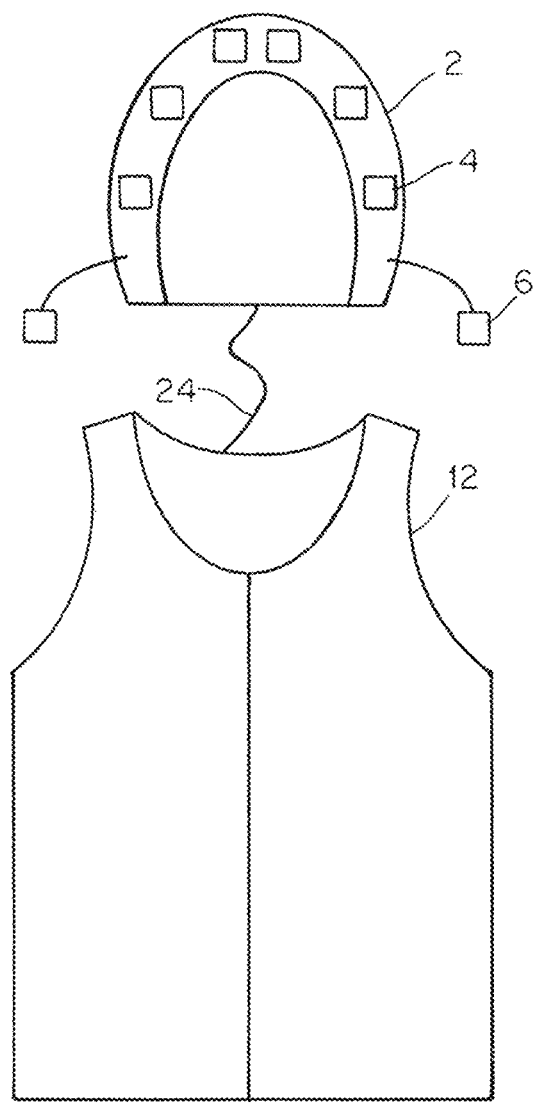
FIG. 1A depicts a front view of a vest and cap including detectors for detecting the presence of a tracer along the spine and in the brain of a subject.

In view of the expense and inconvenience associated with the use of large scale detectors often found in radiology labs, the inventors have recognized the benefits associated with wearable and/or mobile detectors for monitoring the presence, concentration, and/or changes over time in the presence or concentration of one or more tracers within one or more body portions of a subject. Specifically, the inventors have recognized the benefits associated with a medical detector system including a wearable structure that may be worn on a portion of body. The system may also include at least a first detector capable of detecting the presence, concentration, and/or changes over time in the presence or concentration of a tracer. The one or more detectors may be coupled to the wearable structure such that the detector is positioned proximate to the body portion of interest for a subject when the wearable structure is worn. The detector may then be used to detect the presence, concentration, and/or changes over time in the presence or concentration of a tracer within the body portion which may be indicative of, for example, the delivery of a therapeutic compound to the body portion and/or the presence of a medical condition as detailed further below. In some embodiments, such a system may also provide benefits such as functional real time radiological imaging of a subject.

In some instances the body portion being monitored is the brain of a subject. In one such embodiment, detectors are located proximate to the head of a subject for monitoring the presence, concentration, and/or changes over time in the presence or concentration of a tracer within the brain tissue. The one or more detectors may be located around the head in any appropriate arrangement. For example, in one embodiment, it may be desirable to use a configuration of the detectors similar to a electroencephalogram (EEG) detector configuration in order to leverage the familiarity of medical personnel with such a layout as well as visualization techniques and devices used with those layouts. In one such embodiment, the detectors may be arranged in a 10-20 EEG layout. Additionally, depending on the particular embodiment, the detectors may be arranged such that there is a first set of detectors arranged to measure a first hemisphere of the brain and a second set of detectors that measure the second hemisphere of the brain. However, it should be understood that any appropriate arrangement of detectors for monitoring the presence, concentration, and/or changes over time in the presence or concentration of a tracer within either a specific portion and/or the entirety of the brain of a subject may be used.

In another embodiment, it may be desirable to monitor the presence, concentration, and/or changes over time in the presence or concentration of a tracer within the spine or spinal cerebrospinal fluid of a subject. Therefore, in one such embodiment, a medical detector system includes detectors located proximate to the spine of a subject, and the detectors may also be located in a number of different locations. For example, a single, or plurality of, detectors may be located at one or more locations along the spine of the subject. While such an arrangement may be sufficient to monitor the presence, concentration, and/or changes over time in the presence or concentration of a tracer within the spine, in some applications it may be desirable to monitor the pharmacokinetic behavior of a compound within the intrathecal space of the spine. Therefore, in some embodiments, a system may include at least three detectors distributed along a length of the spine to provide different time and position points for evaluating the pharmacokinetic behavior of a tracer and associated compound. In some applications, such as monitoring an intrathecal injection, the detectors may be located between and/or at a lumbar cistern and a cisterna magna of the subject.

While specific numbers and locations of detectors located along the spine of subject are detailed above, it should be understood that any number of detectors may be used in any number of different locations. For example, depending on the embodiment, three detectors, ten detectors, one detector per vertebrae, or any other appropriate number of detectors may be used in a particular system as the disclosure is not so limited. Additionally, depending on what is being monitored, the detectors may be located over, between, or at any other appropriate position relative to the associated vertebrae and/or spinous processes located along the length of a subject's spine.

Specific applications of medical detector systems for monitoring the presence, concentration, and/or changes over time in the presence or concentration of a tracer within the brain and/or spine of a subject are described above. However, in some embodiments, it may be desirable to have a medical detector system that monitors the presence, concentration, and/or changes over time in the presence or concentration of a tracer within both the brain and the intrathecal space of the spine. In one such embodiment, the system may include first and second wearable structures that may be worn on the head and the torso of a subject respectfully. The first and second wearable structures also include detectors for monitoring the presence, concentration, and/or changes over time in the presence or concentration of a tracer within the associated body portion. The first and second structures may form a combined structure such as a vest worn on the torso and an associated hood connected to the vest that is worn on the head of a subject. Alternatively, the first and second structures may be separate structures that are separately worn on the head and the torso of a subject as the disclosure is not so limited.

Depending on the particular embodiment, a wearable structure may correspond to any number of different arrangements for wearing on different body portions. For example, the wearable structure may take the form of a hat, helmet, vest, shirt, cap, shoe, glove, bracelet, sleeve, legging, collar, head band, arm band, leg band, waist band, shorts, pants, body sleeve, corset, or any other appropriate structure, and may include a combination of two or more of any of the foregoing. Correspondingly, the structure may either be a flexible material such as a fabric, or it may be in the form of a rigid shell made from a material such as a bulk plastic or metal. The structures may be attached to the associated body portion using any appropriate method including, for example, the inherent elasticity of a material, straps, elastic bands, snaps, ties, hook and loop fasteners, clips, and/or any other applicable method of attaching and/or fitting the structures to a related body portion.

The currently disclosed systems may be applied to measure the presence, concentration, and/or changes over time in the presence or concentration of tracers within distinct body parts. This can allow optimized tracking of very low signals by placing detectors appropriately on portions of the body close to the locations of interest. For example, appropriate body portions include, but are not limited to, the head, torso, abdomen, arms, hands, hips, legs, feet, neck, and/or subportion thereof. Further, detectors located on these body portions may be used for monitoring the presence, concentration, and/or changes over time in the presence or concentration of tracers within a thyroid, lymph node, salivary gland, eye, deep vein, brain, intrathecal space of the spine, appendix, liver, kidneys, adrenal glands or other appropriate structure of a subject's body. For instance, in one embodiment, one or more detectors are arranged proximate to a subject's neck for measuring tracers in a thyroid and/or neck lymph nodes of a subject. Alternatively, in another embodiment, one or more detectors are arranged proximate to the face cheeks, chin, and/or neck of a subject to measure salivary gland uptake. In yet another embodiment, detectors are arranged proximate to the arm pits and/or groin of a subject for detecting tracers located in the related lymph nodes located in those portions of the body. In another application, a system is designed for monitoring the appendix of a subject and thus includes detectors worn over a right lower quadrant of a subject's torso. Other possible applications include a wearable structure intended to be worn over the calves in the form of a stocking, or similar form, with one or more detectors for monitoring deep vein thrombosis using a tracer, such as a Procrit tracer. Detectors may also be used to monitor the presence, concentration, and/or changes over time in the presence or concentration of tracers adjacent and/or in the eyes of a subject. In such an embodiment, an eyepatch, or similar structure, may be positioned over the eye with one or more detectors to enable the detection of relatively small signals which may aid in detecting drug concentrations, gene expression, and/or biomarkers in age-related macular degeneration (AMD) or other eye disorders. In view of the above, it should be understood, that the presently disclosed systems may be integrated into any number of different wearable structures and may be used for monitoring any number of different body portions of a subject as the disclosure is not so limited.

It should be understood that any appropriate tracer may be used with the presently disclosed systems. For example, a tracer associated with a particular compound of interest may either be a radioactive tracer such as a radioactive isotope, a magnetic tracer, luminescent tracer, and/or a fluorescent tracer. In instances where a fluorescent tracer is used, the system may include an integrated or separate excitation source capable of directing an excitation wavelength towards the body portion of interest in order to generate a fluorescent signal from the associated tracer. In some embodiments, the excitation source may have a wavelength that is in or below the near infrared spectrum (700 nm to 2500 nm wavelengths) such that the excitation source is able to penetrate tissue to excite the fluorescent tracers.

Appropriate detectors for detecting a fluorescent and/or luminescent tracer include but are not limited to, CCD (charged-couple device) and CMOS (complementary metal oxide semiconductor) based detectors, avalanche photo-diodes, as well as others to name a few. In other embodiments, detectors for detecting a magnetic tracer include, but are not limited to, Hall effect sensors, magneto-diodes, magneto-transistors, AMR magnetometers, and/or GMR magnetometers. Lastly, appropriate detectors for detecting a radioactive tracer include, but are not limited to, scintillating materials coupled with an optical detector such as a CMOS or CCD camera, direct conversion devices (i.e. solid state radiation detectors) such as CdZnTe semiconductor detectors, Geeiger-Mueller tubes, or any other appropriate detector. In one particular embodiment, a detector includes a CMOS chip where the control of the CMOS chip has been adapted to directly sense and convert an emission from at least a first radioactive tracer into a detectable signal similar to other solid state radiation detectors without the need for a scintillating material or other device for converting the radiation into an optical signal first.

In some instances, it may be desirable to adjust for the differences in size of various individuals when positioning a wearable medical detector system on a subject. Depending on the particular embodiment, this adjustability may be provided by either the elasticity of a structure associated with the body portion, adjustable components such as straps and fasteners, adjustable detector positions, and/or any other appropriate arrangement or feature. Alternatively, in other embodiments, different sizes of a wearable medical detector system may be used for different size individuals. For example, a range of sizes of a particular system may be provided for accommodating different body types ranging from adults to children, short to tall individuals, slim to overweight or obese individuals, or any other range of body types as the disclosure is not so limited.

For purposes of this disclosure, the term wearable includes a structure capable of being worn or carried on the body of an individual similar to an item of clothing. Depending on the particular embodiment, the wearable device may provide freedom of movement for a subject wearing the systems due to the use of wireless connections, visual indicators, a power source (e.g. batteries, capacitors, wireless power transmission, etc.), and/or storage for later download of detected information. However, embodiments in which a medical detector system includes one or more wearable structures, has a wired connection to a controller and/or storage device, or otherwise limits the movement of a subject are also contemplated as the disclosure is not so limited.

Therapeutic compounds for purposes of this application may correspond to any appropriate material including, but not limited to, any drug, medication, pharmaceutical preparation, contrast agent, and/or biologic such as a protein, antisense molecule, and gene therapy viral vector as the disclosure is not so limited. Further, a tracer associated with a therapeutic compound may be bonded to the therapeutic compound using any appropriate method known in the art. It should be understood that the specific amount and effect will vary depending on the particular therapeutic compound being used. Additionally, as will be appreciated by one of skill in the art, the therapeutic compounds described herein may be provided in any number of different forms including, but not limited to, suspensions, liquids, slurries, powders, nanoparticles, and/or gels. When a therapeutic compound is present in a particular location in an "effective amount" it means a concentration of the therapeutic compound is greater than or equal to a trace amount and is sufficient for achieving a desired purpose, such as, for example, to permit detection of the compound in a subject for diagnostic purposes, to treat a disease or condition in a subject, and/or enhance a treatment of a disease or condition in a subject. In some embodiments, an effective amount of a particular therapeutic compound is present in an amount sufficient to reduce or alleviate one or more conditions associated with a particular condition (e.g., neuropathic pain, primary brain or metastatic cancer, neurodegenerative disease, neurogenetic disease, neuro-infections). In another embodiment, the therapeutic compound is a diagnostic compound such that its presence at a particular location is indicative of a particular condition of a subject. As noted previously, the therapeutic compounds may be conjugated with a detectable moiety to enable the presently described detectors to detect their presence. For example, a detectable moiety may be a radioisotope, magnetic particle, luminescent molecule, or fluorescent dye as the disclosure is not so limited. It should be noted that in the case of radioactive tracers, the tracers selected for a particular application and duration of monitoring should have a sufficiently long half-life to provide a detectable signal throughout the monitoring period. Due to different tracers having different half-lives, one of skill in the art may select an appropriate tracer based both on its ability to be conjugated with a compound as well as its half-life versus the time period monitoring will be conducted over.

Based on the above, it should be understood that a medical detector system as disclosed herein may be used for any number of applications. However, in one embodiment, a medical detector system may be used to detect the presence, concentration, and/or changes over time in the presence or concentration of a therapeutic compound at a particular body portion. In one such embodiment, the therapeutic compound is a diagnostic compound conjugated with a detectable moiety, as noted above, such that its presence and/or concentration as detected by the medical detector system may be used to identify a medical condition. Alternatively, in another embodiment, a therapeutic compound may be used to treat a particular condition. Therefore, in one embodiment, a medical detector system may be used to detect the presence, concentration, and/or changes over time in the presence or concentration of the therapeutic compound to either insure that an effective amount of the therapeutic compound has reached the target location and/or that treatment should continue until an effective amount of the therapeutic compound has reached the target location. For example, a medical detector system may include detectors distributed along both a spine and about the head of a subject such that the detectors may monitor the progress of a therapeutic compound as it disperses from the injection site along the intrathecal space and into the brain tissue of a subject. Of course, while several possible applications are detailed above, it should be understood that other applications for the presently disclosed medical detector systems are also contemplated as the disclosure is not limited to any specific application.

Turning now to figures, several specific embodiments are described in further detail. For example, medical detector systems including detectors for detecting the presence, concentration, and/or changes over time in the presence or concentration of tracers within the head, spine, and/or an extremity of a subject are described. However, it should be understood that systems including other wearable structures and/or detectors located adjacent to other body portions are also contemplated as previously described. Consequently, the present disclosure should not be limited to only the embodiments described in the figures and should instead be interpreted broadly as encompassing any of the systems, features, as well as individual portions and/or combinations of the various embodiments described herein as the disclosure is not so limited.

Figure 1B:
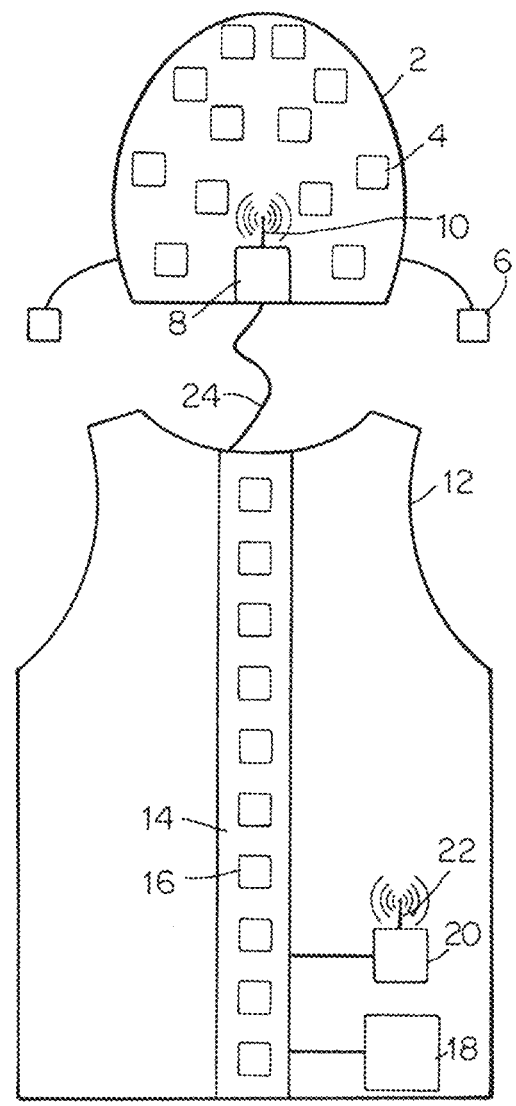
FIG. 1B depicts a schematic rear view of a vest and cap including detectors for detecting the presence of a tracer along the spine and in the brain of a subject.

FIGS. 1A and 1B depict an embodiment of a medical detector system including two separate wearable structures corresponding to a cap 2 wearable on a head of a subject and a vest 12 wearable on a torso of the subject. The functionality of the cap and the vest which include one or more detectors is described further below.

The depicted cap 2 includes a plurality of detectors 4 distributed around and coupled to the cap to measure the presence, concentration, and/or changes over time in the presence or concentration of a tracer within different locations of the brain for a subject wearing the cap. In some embodiments, the cap includes one or more additional detectors 6 connected to the cap by a flexible connection such that these additional detectors may be positioned on another portion of the subject such as a cheek, forehead, and/or throat of the subject. The cap also includes one or more controllers 8 in communication with the detectors 4 and 6 to readout the counts and/or images provided by each detector. Depending on the particular embodiment, the controller may either simply read out a signal provided by the detectors, or it may also control the collection and timing of signals from the detectors, as the disclosure is not limited to any particular type of control scheme for the detectors.

The vest 12 depicted in the figures is a simple construction that may either be slipped on the torso of a subject and/or the vest may include an openable seam for easily donning the garment by a subject. To close the openable seam, the vest may include appropriate closure mechanisms such as buttons, ties, zippers, hook and loop fasteners, and the like, not depicted. While a vest with an openable seam has been depicted, other appropriate structures for wearing on a torso of a subject may also be used.

As illustrated in the figures, a vest 12 may also include one or more detectors 16 coupled to the structure for detecting the presence, concentration, and/or changes over time in the presence or concentration of a tracer within the intrathecal space of a spine of a subject. In one such embodiment, a plurality of detectors are distributed along the spine of the subject. Similar to the cap, the vest 12, or other similar wearable structure, also includes a controller 20 in communication with the one or more detectors 16 of the vest in order to readout the counts and/or images provided by each detector as well as possibly controlling the detectors as noted previously.

In some instances, it may be desirable to help stabilize the detector positions relative to the spine by including a support 14 attached to the vest. The support may also be associated with the plurality of detector such that it extends along a direction of the plurality of detectors as well as along the spine of the subject when the vest, or other wearable structure, is worn by the subject. To provide the desired stiffness, a stiffness of the support is greater than a stiffness of the wearable structure in at least a direction parallel to an exterior surface of the vest, or other wearable structure. For example, in one specific embodiment, a vest is made from a stretchable neoprene material and the support is a laminated strip of vinyl material that is stiffer in the plane of the material. The strip of vinyl extends from a bottom edge to a top edge of the vest along the spine of a subject wearing the vest. Therefore, the laminated vinyl support strip may help to avoid movement of the detectors relative to the spine both in the up down as well as the side to side directions.

While the above described detectors have been depicted as being coupled to an exterior surface of the associated wearable structures, the current disclosure is not so limited. Instead, the presently disclosed detectors may be coupled to a structure such that they are disposed on an interior surface, exterior surface, within the wearable structure, or at any other appropriate location relative to the wearable structure.

To enhance mobility as well as provide for possible smart functionality, it may be desirable to provide a wireless connection for remotely controlling the detectors and/or downloading information received from the various detectors. In such an embodiment, a transmitter 10 associated with the cap and/or a transmitter 22 associated with the vest are in communication with their respective controllers 8 and 20 as well as the associated detectors. Therefore, images and/or counts corresponding to detected signal emissions from at least one tracer located in a portion of the body may be transmitted by the one or more depicted transmitters to a separate processing device such as a server, computer, tablet, smart phone, and/or any other appropriate device. In some embodiments, the processing device is a remotely located processing device. For example, in one such application, information may be transmitted from a medical detector system to a cloud-based storage server and/or to another database or system accessible by medical personal overseeing a medical condition or procedure for the subject being monitored by the medical detector system. Alternatively, or in addition, onboard computer memory such as flash memory, EEPROM memory, solid-state memory, or any other appropriate memory device may be used to store information from the one or more detectors for subsequent download by a physical link as the disclosure is not so limited. It should be understood that while transmitters associated with the individual controllers located on the separate structures has been depicted in figures, in other embodiments, a transmitter located on a wearable structure may be in communication with detectors located on another separate wearable structure either via a hardwired or wireless link such that the transmitter is capable of transmitting information related to both sets of detectors located on the separate wearable structures to a separate processing device. Of course, embodiments in which the processing device is incorporated into one or more of the wearable structures are also contemplated.

In some embodiments, a medical detector system is intended to be used in a mobile application. In such an embodiment, a system may include one or more batteries 18. While individual batteries may be included in the wearable structures of the system, in one embodiment, one or more batteries are located on a portion of the system worn on the torso of a subject, such as the vest 12 depicted in FIG. 1B. Further, the batteries may be located on a region of the vest, or other structure worn on the torso, to help distribute the weight of the batteries to the hips of a subject. In embodiments where individual batteries are not included in each wearable structure, an electrical connection may extend between two or more separate wearable structures to provide power to the corresponding controllers and detectors. For example, an electrical connection 24 may extend from the vest 12 to the cap 2 to provide electrical power to the cap even though the cap includes two separate transmitters. However, it should be understood that batteries may be positioned at any region of a structure as well as at locations other than the torso of a subject as the disclosure is not so limited. Further all of the depicted components including the detector, controller transmitter, and/or battery may be located outside, inside, and/or within a wearable structure as well.

Figure 2:
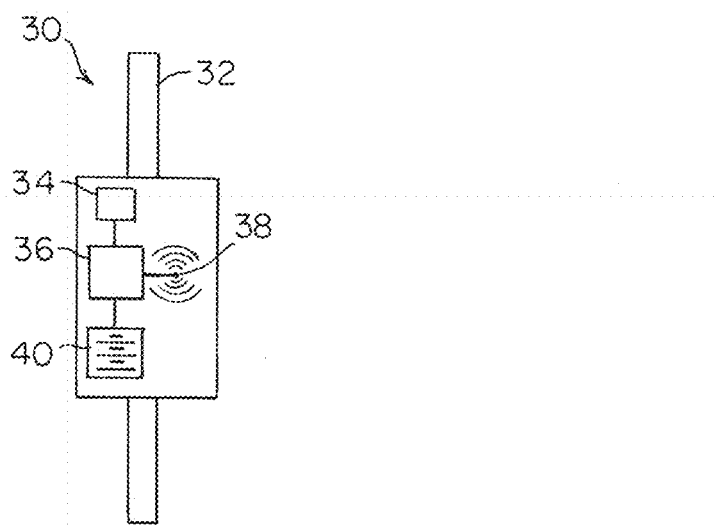
FIG. 2 depicts a bracelet including a detector for detecting the presence of a tracer in an extremity of a subject.

In some applications including, for example, monitoring of the pharmacokinetics of a compound conjugated with a tracer, it may be desirable to normalize the signal detected by one or more reference detectors associated with a given body portion to account for signal counts arising from compounds located within the blood not the tissue of a region. In one such embodiment, the detected signals are normalized using the signal detected at an extremity of a subject's body which is removed from the location of interest. Appropriate extremities include, but are not limited to, an ankle, wrist, arm, leg, or any other appropriately located portion of a body removed relative to an area of interest. One such device is shown in FIG. 2 which depicts a wearable structure in the form of a bracelet 30. The bracelet includes a pair of straps 32 that are attached to one another using any appropriate form of coupling such as a clips, buttons, magnets, and/or touch fasteners. Using these straps, the device may be attached to an extremity of the body such as the wrist or ankle of a subject. Similar to the other wearable structures including detectors described above, the bracelet includes one or more detectors 34 for sensing the presence, concentration, and/or changes over time in the presence or concentration of one or more tracers as well as a controller 36, optional transmitter 38, and battery 40, the operations of which are described above.

The tracer signal from an extremity of a subject may be used to normalize detector signals in any number of ways. In the simplest embodiment, a signal from the reference detector is simply subtracted from the signals from the other detectors. In another embodiment, the signal corresponding to a tracer within the blood of the extremity may be scaled by the ratio of the blood volumes located in the extremity and location of interest. The scaled signal may then be subtracted from the signals of the other detectors. Of course, it should be understood that other techniques for normalizing a signal may also be implemented as the disclosure is not so limited. Normalization of the signal may also take into account background radiation which may be detected either with a separate detector, and/or the detector described above located on an extremity of a subject.

In the above embodiments, the use of wireless transmitters have been described for use with the presently disclosed medical detector systems. However, the disclosure is not limited to only wireless transmitters. For example, hard-wired connections to one or more of the wearable structures including detectors may also be used. Further, in some instances it may also be desirable to include a receiver in communication with the controller of a medical detector system for receiving uploaded information such as commands from an externally located processing device such as a computer or server, a time information, location information, or any other information that may be of use with a medical detector system. For example, commands communicated back to the controller of a detector system may include altering the active versus inactive state of the detectors (i.e. turning the detectors on and off), adjusting measurement thresholds, applying signal filters, altering measurement frequency, altering measurement parameters (e.g. integration time), and/or any other appropriate control parameter for controlling the use of a medical detector system. While in some instances a separate receiver may be used, in other embodiments, the described transmitters above may act as both transmitters and receivers as the disclosure is not limited to how transmission and reception of signals is specifically implemented on a device.

Figure 3A:
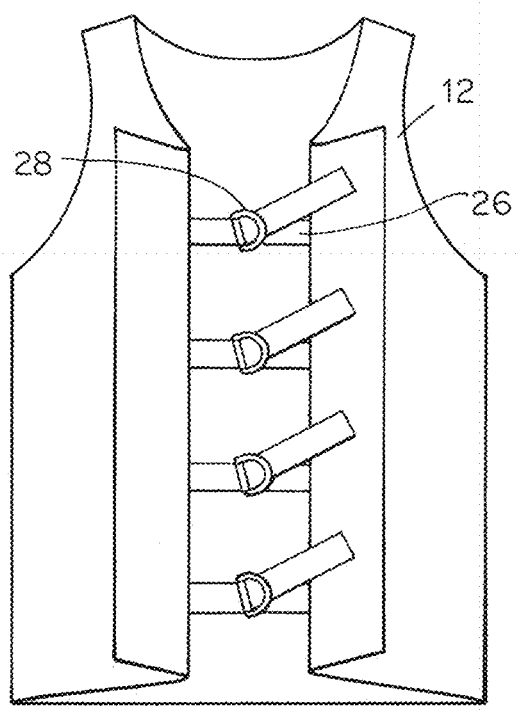
FIG. 3A depicts a schematic front view of a vest including straps for maintaining a support and associated detectors proximate the spine of a subject.
Figure 3B:
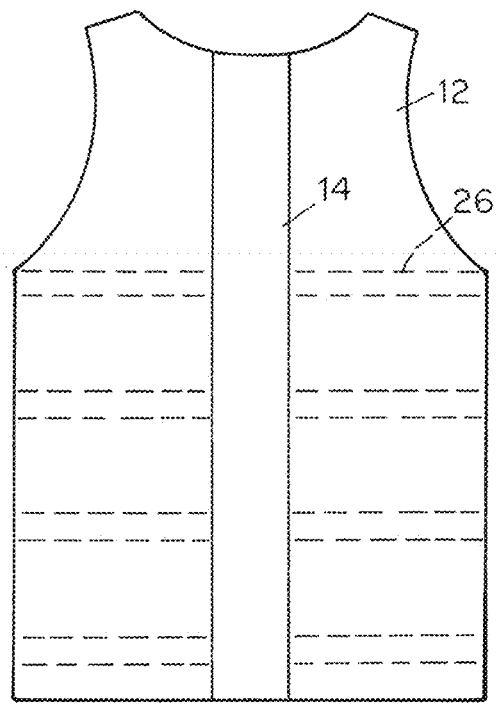
FIG. 3B depicts a schematic rear view of a vest including straps for maintaining a support and associated detectors proximate the spine of a subject.

In order to enhance the reliability, repeatability, and sensitivity of a medical detector system as described herein, it may be desirable to maintain the positioning of detectors proximate to a desired location being monitored. FIGS. 3A-3B depict one embodiment of structure for maintaining a plurality of detectors proximate to a portion of the body of a subject. In the depicted embodiment, the wearable structure is a vest 12 including a support strip 14 extending along the spine of the subject when the vest is worn as described above. For the sake of clarity, the detectors positioned along the spine of the subject and the support strip of the vest have not been depicted. The structure includes one or more adjustment devices 26, which in the depicted embodiment are a series of straps, attached to the wearable structure in any appropriate fashion. For example, the straps may be sown, bonded with adhesive, ultrasonically welded, attached through loops, or otherwise attached to the structure. Additionally, the straps may either be attached to the structure at an end of the straps, a middle portion of the straps, or at multiple locations along a length of the straps as the disclosure is not so limited. When tightened, the one or more straps maintain the plurality of detectors proximate to the spine of the subject when the wearable structure is worn by the subject. Depending on the particular embodiment, the straps may be tightened either by adjusting a length of the straps using opposing adjustable ends of the straps connected by connectors 28, or the straps may be elastic and have a sufficiently short unstretched length, that the straps are placed in tension when the structure (i.e. vest) is worn. Once the straps are tightened, they apply a force to the detectors and/or the associated support strip 14 that bias the plurality of detectors so that they are maintained proximate to the location of interest, such as the spine, of the subject's body.

It should be understood that while the adjustment devices depicted in the figures have been shown located on the inside of a vest, the adjustment devices may be located either inside, within, or on the exterior of a wearable structure as the disclosure is not so limited. Additionally, in some embodiments, a plurality of adjustment devices, such as a plurality of straps, may be distributed along a length of the wearable structure to maintain the position of a plurality of associated detectors relative to a specific body portion of a subject such as the spine. For example, a plurality of adjustment devices may be distributed along the length of a wearable structure such in a direction extending along the subject's spine toward the subject's head. Depending on the particular embodiment 1, 2, 3, 4, or any number of adjustment devices may be used to help maintain a plurality of detectors at a desired position.

While the adjustment devices described above have primarily been directed to the use of various types of straps, the disclosure is not limited to only straps. For example, appropriate adjustment devices may include: pull cords; laces; regions with a series buttons or snaps for controlling the amount of loose material; elastic zones integrated in the wearable structure; or any other appropriate combination of features capable of maintaining the positioning and/or alignment of the detectors relative to a desired body portion.

Figure 4:
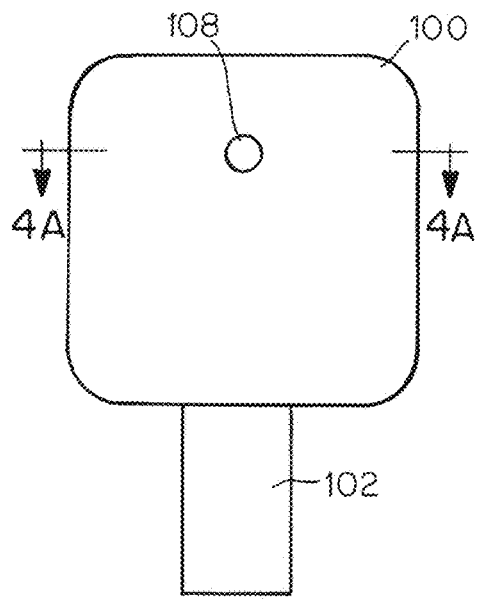
FIG. 4 depicts a front view of a detector.
Figure 5:
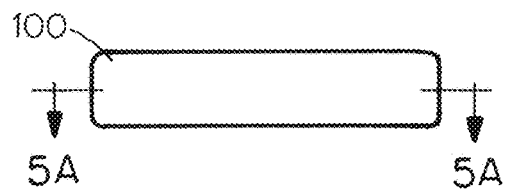
FIG. 5 depicts a side view of a detector.
Figure 4A:
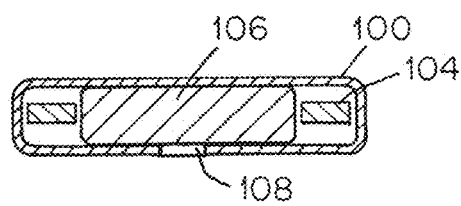
FIG. 4A depicts a cross sectional view of the detector of FIG. 4.
Figure 5A:
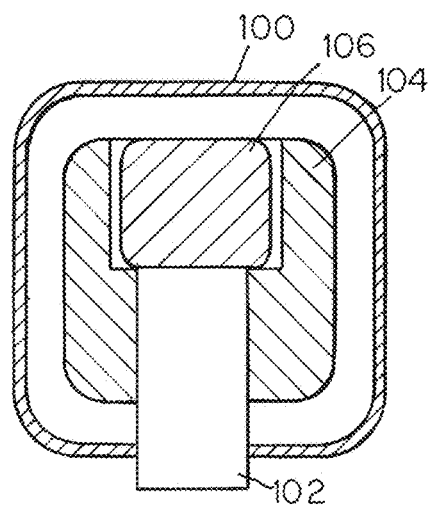
FIG. 5A depicts a cross sectional view of the detector of FIG. 5.

FIGS. 4-5A depict an embodiment of a detector 106 disposed within a housing 100. As noted previously, the detector may correspond to any appropriate detector capable of sensing the presence, concentration, and/or changes over time in the presence or concentration of a tracer using light, radiation, and/or magnetic based sensors. However, in at least one embodiment, the detector is a CMOS chip aligned and positioned within the housing interior by one or more supports 104. Signals may be output from the detector to a corresponding controller via a cable 102. It should be understood that a wireless connection between a detector and controller may also be used as the disclosure is not so limited.

The detectors and associated housings depicted in the figures may be attached to a corresponding wearable structure in any appropriate manner including either a fixed connection and/or a repositionable connection. For example, a detector 106 located within a housing 100, as described above, may be coupled either directly, or indirectly, to a corresponding wearable structure in any appropriate manner including, but not limited to, snaps, hook and loop fasteners, adhesives, ultrasonic welds, mechanically interlocking features, bolts, and/or rivets. Alternatively, in another embodiment, a detector may be directly attached to the wearable structure without a separate housing located there between. However, it should be understood that the current disclosure is not limited to the depicted embodiments of detectors located within housings and/or directly attached to a structure because any number of different arrangements and methods for attaching one or more detectors to a structure may be used. In one such alternative embodiment, a plurality of detectors are integrated in a flexible circuit board such that the detectors are attached to, or integrated with, the flexible circuit board. The flexible circuit board is then attached to the corresponding wearable structure to appropriately position the detectors about the flexible structure. In addition to ease of assembly, such an embodiment provides the additional benefit of not requiring separate control cables for connecting detectors to associated controllers.

In some embodiments, a detector housing may be transparent to the emissions of a particular tracer. For example, the housing may be transparent to fluorescent emissions and/or radiation emitted by a tracer. Alternatively, in other embodiments, it may be desirable to prevent emissions from being sensed by a detector in directions other than those oriented towards a desired portion of a subject's body. In such an embodiment, the housing may be made from a material that is opaque to the emissions of a particular tracer. In one such embodiment, the tracer is a radioactive isotope and the housing is radiopaque to the emitted radiation. In order to permit the detector to detect emissions from the tracer, the housing may include one or more apertures 102 aligned with a portion of the detector sensitive to the noted emissions. The apertures may either correspond to openings in the housing and/or windows made from material that is transparent to the emissions from the tracer. Such an arrangement will limit the angle of acceptance of the detector to emissions located within the field of view through the aperture.

Figure 6:
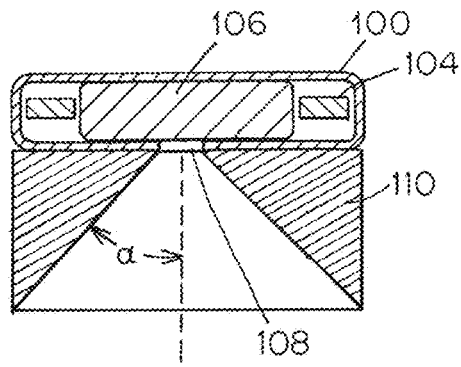
FIG. 6 depicts a cross sectional view of a detector including a shielded housing and exhibits angle discrimination.

In some embodiments, it may be desirable to further limit the angle of acceptance for a detector when used for some applications. This may be of particular benefit in applications such as limiting the area of detection to a specific location or structure and/or when performing computed tomography. One possible embodiment of a device for limiting the angle of acceptance is shown in FIG. 6 where a collimator 110 is either integrally formed with, or otherwise attached, so that it forms a part of the housing 100. Alternatively, the collimator may be indirectly associated with a detector as the disclosure is not so limited. Regardless, in the depicted embodiment, the collimator limits an angle of acceptance α of the detector 106. While a generic collimator has been depicted, any number of types of collimators may be used depending on the type of emission being detected. Appropriate collimators for use with radioactive tracers include, but are not limited to, parallel hole collimators, slant hole collimators, converging and diverging collimators, fan-beam collimators, as well as pin hole collimators such as the cone shaped arrangement depicted in the figure. Depending on the application, a collimator may restrict the angle of acceptance of a detector to an angle α that is less than or equal to 60°, 45°, 30°, and/or 15°. However, angles both larger and smaller than those noted above are also contemplated.

Figure 7:
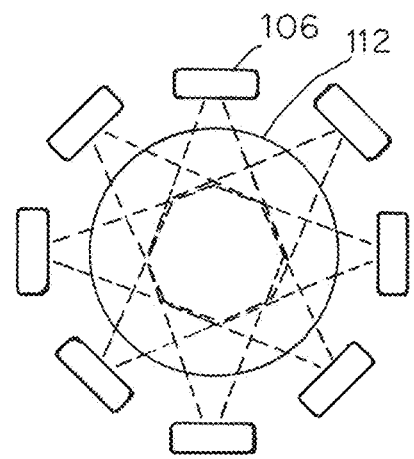
FIG. 7 depicts a schematic layout of detectors arranged with overlapping angles of acceptance for performing computed tomography.

FIG. 7 depicts one application of a plurality of detectors 106 including an angle of acceptance α for use in computed tomography. As depicted in the figure, the detectors are arranged around the exterior of body portion 112. The body portion may correspond to any appropriate body portion, including, but not limited to a head, arm, torso, or leg of a subject. Further, the detectors may be attached to a wearable structure worn on the body portion, not depicted, as described herein for maintaining the detectors proximate to the body portion. In addition to the above, the detectors are positioned so that they have overlapping fields of view as illustrated by the acceptance angles depicted in the figure. This arrangement of detectors facilitate detecting and locating the source of emissions, such as radiation, emitted by a tracer located within the body portion. Specifically, the signals detected by the individual detectors are output to a processor using any appropriate method and are then used to form a computed tomography image or signal intensity mapped onto the body portion which may then be used to evaluate the presence, concentration, and/or changes over time in the presence or concentration of a tracer within a sub part of the body portion being monitored. For example, detectors arranged around the head of a subject may have angles of acceptance directed towards a portion of the brain that is of interest for a particular diagnostic or therapeutic procedure. Therefore, when a signal above a threshold level is detected in a particular brain structure of interest using computed tomography, it may indicate the presence of a medical condition and/or that a therapeutically effective amount of a compound has reached the region of interest. Such an arrangement may also be used to do functional real time imaging of a subject.

Figure 8:
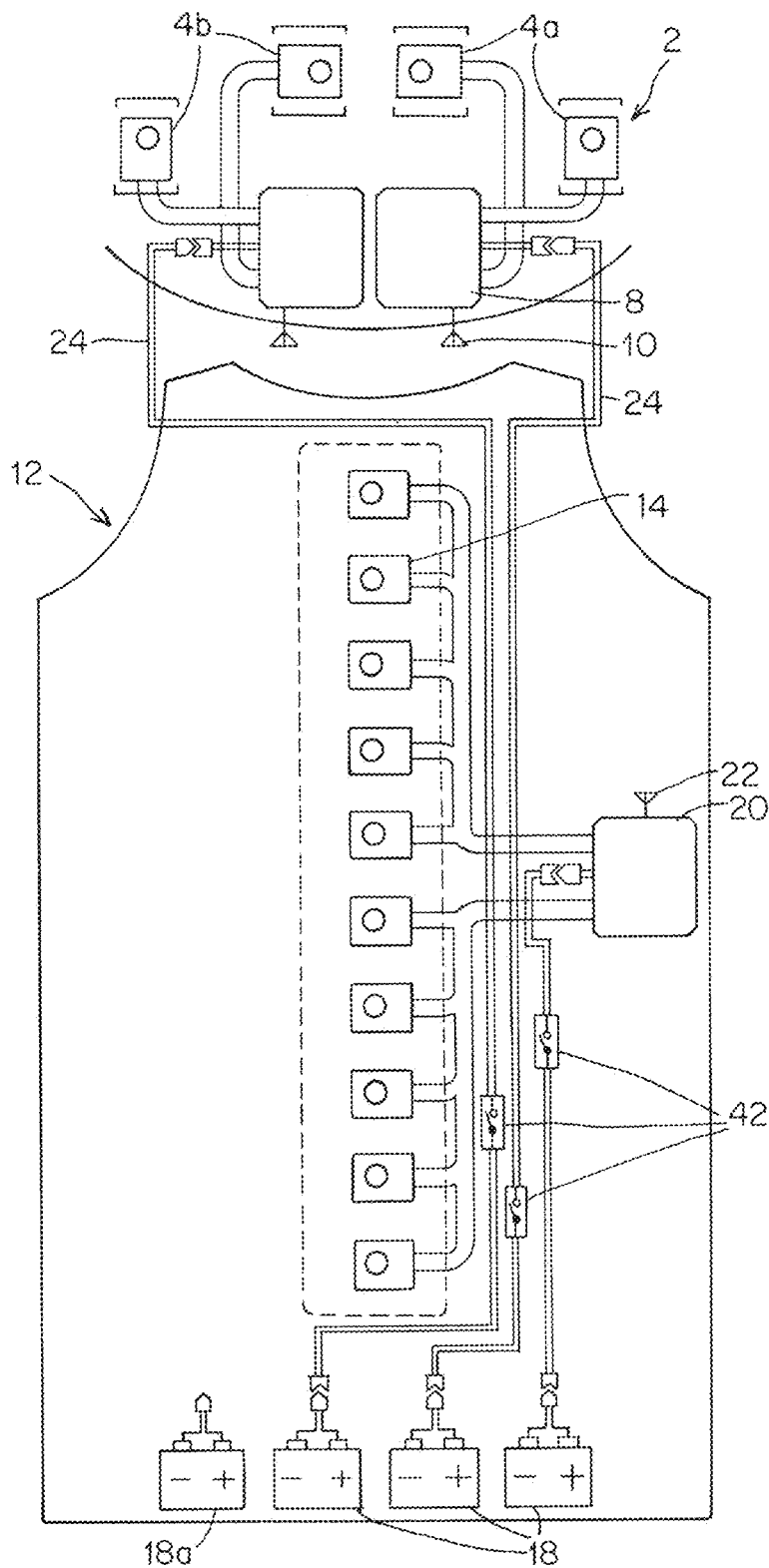
FIG. 8 depicts the electrical layout of a medical detector system including detectors along the spine and on the head of a subject.

FIG. 8 presents a schematic electrical layout for a medical detector system including detectors arranged on two separate wearable structures corresponding to a cap 2 and vest 12. While two distinct and separate wearable structures have been illustrated, it should be understood that the two wearable structures may either be separate as shown or integrated into a single structure as the disclosure is not so limited. As illustrated in the figure, the cap includes two separate controllers 8 which are in communication with two separate transmitters 10 and two separate sets of detectors 4a and 4b which have ten detectors each. However, it should be understood that different numbers of detectors, transmitters, and controllers may be used. In the depicted embodiment, the different sets of detectors correspond to different hemispheres of the brain when the cap is worn on the head of a subject. Similarly, the vest 12 includes a plurality of detectors 14 distributed along a spine of a subject and are in communication with a corresponding controller 20 which also includes a transmitter 22 as described above. Batteries 18 are positioned on the hips of the vest and are separately connected to the individual controllers 8 and 20 associated with the detectors 14 located along the spine as well as detectors 4a and 4b located for monitoring different hemispheres of the brain. Again, an electrical connection 24 extends between the vest and the controllers 8 located within the cap. Switches 42 may be located between the batteries and associated controllers in some embodiments in order to turn the devices on or off. In some embodiments, a spare battery 18a is provided on one or more the wearable structures in order to provide power redundancy in case a particular battery is dead. In such an instance, the connection between a battery and associated control may be switched to the spare battery instead.

Figure 9:
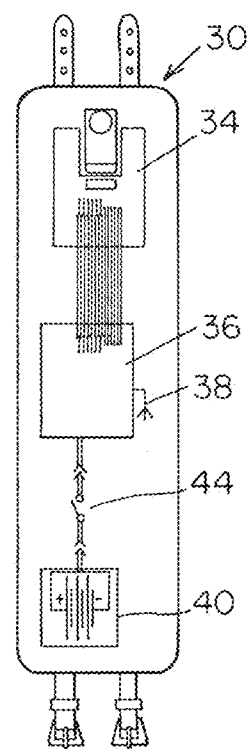
FIG. 9 depicts the electrical layout of a bracelet including a detector for detecting the presence of a tracer in an extremity of a subject.

FIG. 9 depicts a schematic electrical layout of a detector system for monitoring the presence, concentration, and/or changes over time in the presence or concentration of a tracer within an extremity of a subject. As previously described, the system includes a detector 34, controller 36, transmitter 38, and associated battery 40 the operations of which have been previously described. Further, similar to the above, the detector system may also include a switch 44 positioned between the battery and controller in order to control the on off state of the detector device.

Figure 10:
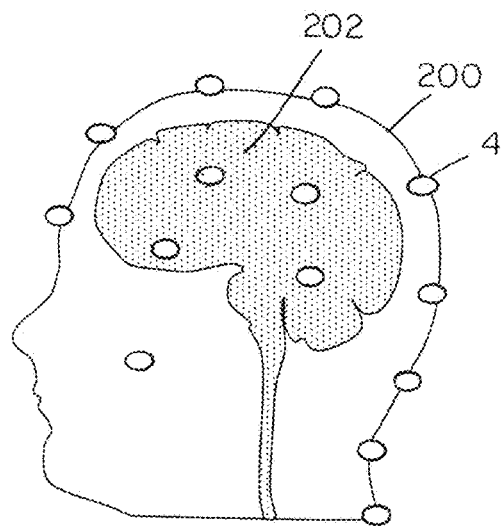
FIG. 10 depicts detectors distributed around the head of a subject.

FIG. 10 illustrates a plurality of detectors 4 positioned around the head 200 of a subject for monitoring the presence, concentration, and/or changes over time in the presence or concentration of one or more tracers within the brain 202 of a subject. However, in some embodiments it may be desirable to supplement and/or substitute these detectors with other detectors associated with the head or other portion of a subject's body such as the esophagus and/or gastrointestinal tract of a subject. Several possible embodiments of various detector arrangements are described further below in regards to FIGS. 11-13.

Figure 11:
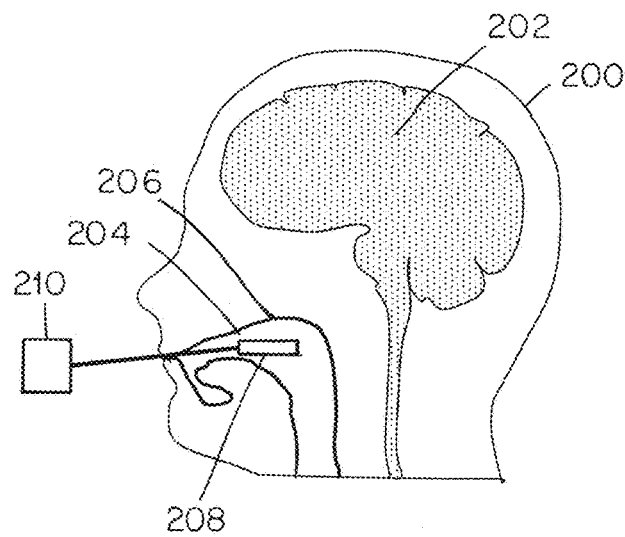
FIG. 11 depicts a detector positioned and held in the mouth of a subject for detecting the presence of a tracer in the brain.

FIG. 11 depicts one embodiment of a detector 208 that is sized and shaped to be positioned in the mouth of a subject which may offer the benefit of providing a detector relatively close to the base of the brain. To provide such a device, the detector may be disposed on, and/or within, a structure that is sized and shaped similar to a dental retainer such that a person may position and hold the structure in their mouth. In such an embodiment, the structure may cover one, or both, of the hard palate 204 and soft palate 206 of the subject and may optionally engage with the teeth of a subject when it is positioned in a subject's mouth. Further, the detector may include a built in controller as well as an associated battery and transmitter. However, as depicted in the figure, instances where a controller 210 and other components are connected to the detector 208 such that they are positioned outside of the mouth of a subject are also contemplated. In addition to being positioned within the mouth of a subject, the detector may also include a radiopaque housing with at least one aperture directed towards a brain of the subject when positioned in the subject's mouth that to limit the detection of emissions from a tracer to signals originating within the brain of a subject. In some embodiments, the one or more apertures may be directed towards a base portion of the brain to facilitate monitoring the presence, concentration, and/or changes over time in the presence or concentration of tracers within that limited section of the brain.

Figure 12:
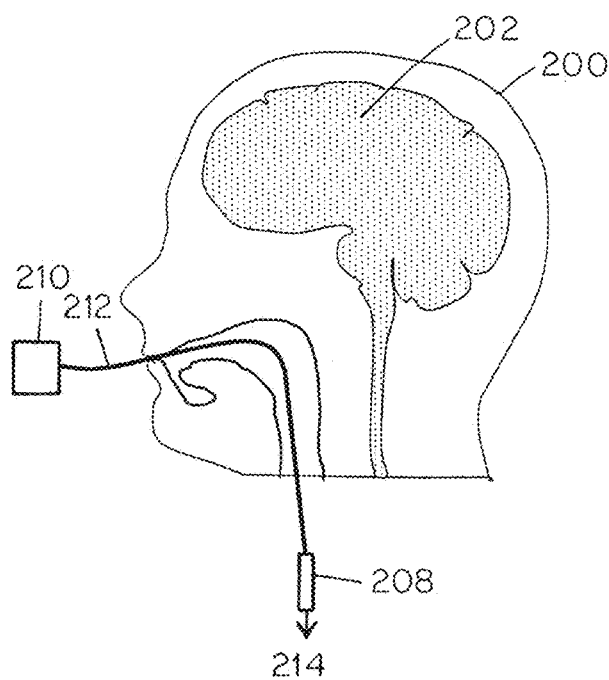
FIG. 12 depicts a detector held in place by a tether within the esophagus or gastrointestinal tract of a subject.

FIG. 12 presents another embodiment of a detector 208. In the depicted embodiment, the detector is swallowed by a subject such that it is located within the esophagus or gastrointestinal tract 214 of the subject. The detector is held in place using a flexible tether 212 that is connected to the detector. The flexible tether passes up to, and in some embodiments, out through the nose or mouth for holding the detector in place. In some instances where the tether does not pass out of the nose or mouth, the tether may be attached to a tooth or to a structure inserted into the mouth or nose of a subject to hold the detector in place. In some embodiments, a detector may include both the components sensitive to emissions from the tracer as well as the various controllers and power sources needed for operating the detector. However, as depicted in the figures, in other embodiments, a separate controller 210 and/or an associated power source may be removed from the detector may also be used. In such an embodiment, the controller may be electrically coupled to the detector via conductive elements present in the tether. While probes on tethers have been described above, in some embodiments, it may be desirable to integrate one of the above noted detectors into an internal medical device probe as might be mounted on a catheter, laparoscope, and/or endoscope including, for example, bronchoscopy and/or colonoscopy probes.

Figure 13:
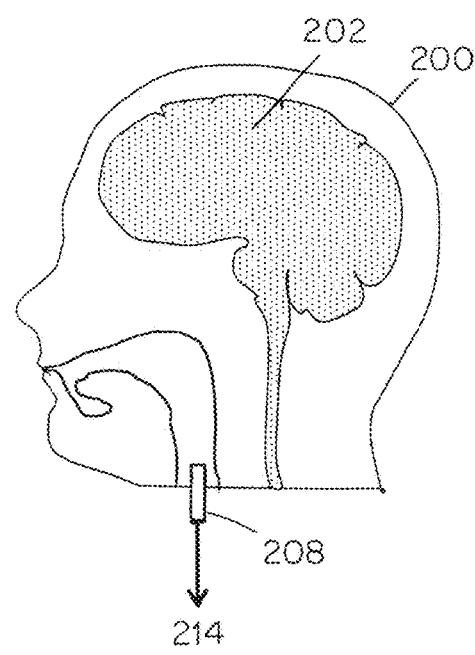
FIG. 13 depicts a detector that is swallowed and passed through the gastrointestinal tract of a subject.

FIG. 13 depicts yet another embodiment of a detector 208. In the depicted embodiment, the detector is a self-contained swallowable wireless detector that measures counts associated with emissions from a desired tracer as it passes through the gastrointestinal tract 214 of a subject. In such an embodiment, the detector includes both the components sensitive to emissions from a tracer as well as a controller, power source, and wireless transmitter contained within a housing of the swallowable detector.

In some embodiments, it may be desirable for the above described detectors and systems to be capable of sensing the presence, concentration, and/or changes over time in the presence or concentration of two or more different tracers such as two different radioisotopes. Such a system may beneficially be used for multiple different applications without the need to tailor the device to a specific therapy or tracer. Additionally through the use of multiple types of detectors on a single wearable device, it may be possible to simultaneously measure two or more different types of tracers including two or more of a radioactive tracer, a fluorescent tracer, and a magnetic tracer.

In other embodiments, it may be desirable for a system to include detectors capable of discriminating between two or more different tracers such as two different radioisotopes. Such a system may be used to facilitate any number of different diagnostics or therapies. For example, multiple therapeutic compounds may be administered at once with at least two of the therapeutic compounds having different tracers which may then be separately monitor by the system. This may result in reduced numbers of procedures and/or lower radiation doses for a particular subject. One such application includes multiplexed detection of brain proteinopathies using multiple therapeutic compounds administered at once to provide enhanced screening and diagnosis of diseases. In another possible application, two or more radioligands may be used simultaneously where one corresponds to a drug (e.g. radiolabeled API) and the second corresponds to a compound suitable for assessing cerebrospinal fluid kinetics (e.g. a hydrophilic radioligand such as [99mTc]-DTPA). However, it should be understood that detectors capable of discriminating between different tracers may be applied to any number of other applications as the disclosure is not limited to only these particular applications.

Figure 14:
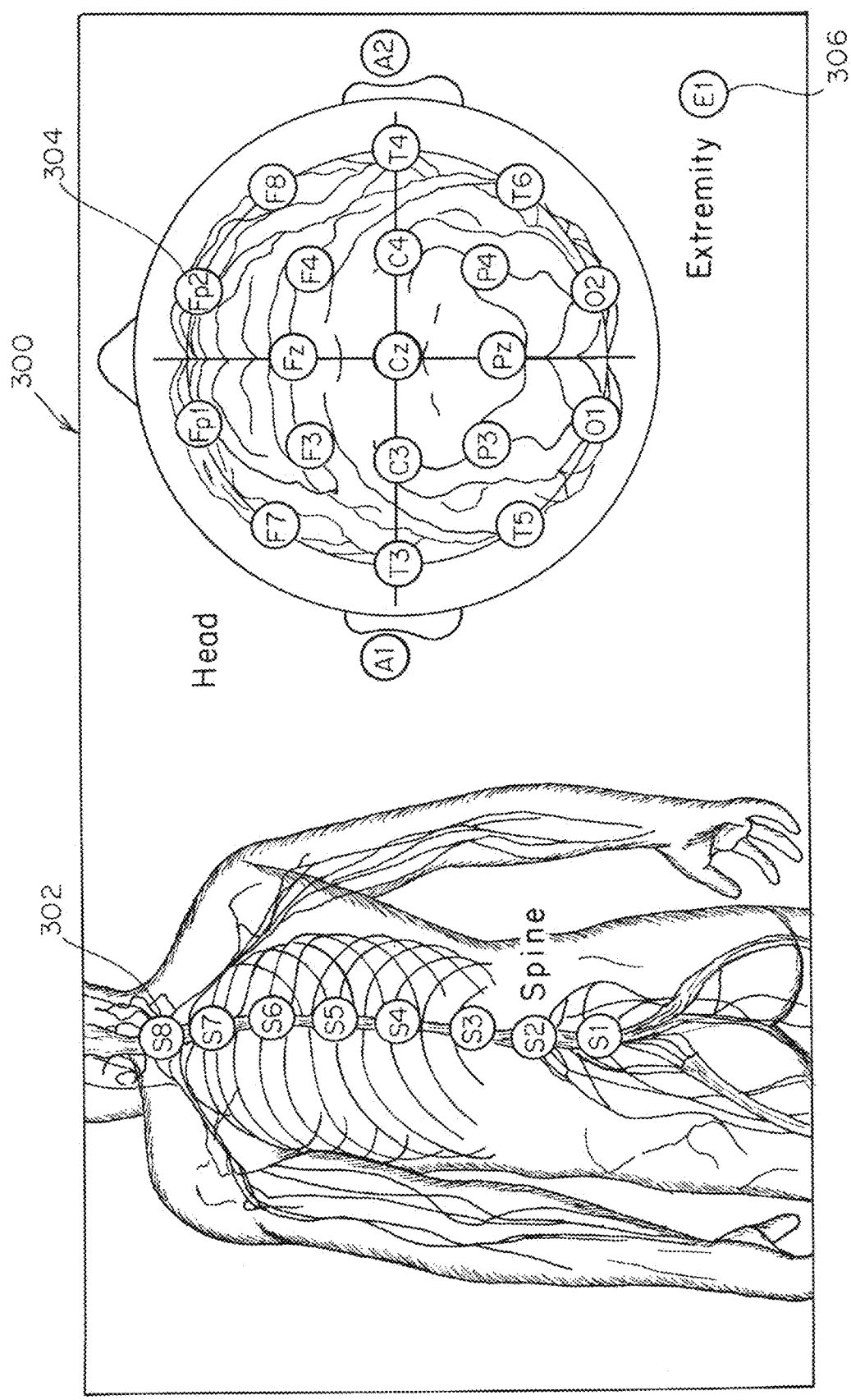
FIG. 14 depicts a graphical user interface for presenting information regarding the presence of a tracer along the spine and in the brain of a subject.

Having described the various detectors and systems for monitoring the presence, concentration, and/or changes over time in the presence or concentration of a tracer within a desired body portion, in some embodiments, it may also be desirable to provide an indication of the detected tracer to a subject, medical personal, or other individuals of interest. For example, in one embodiment, a graphical user interface (GUI) 300 is presented on an appropriate display such as a computer screen, tablet, or a smart phone. As shown in FIG. 14, the GUI includes a plurality of indicators representing the various detectors positioned proximate to the portions of the subject's body. For example, a plurality of indicators 302 correspond to detectors located along the spine of the subject while indicators of 304 correspond to detectors positioned around the head the subject. The GUI also includes an indicator 306 corresponding to a detector located on an extremity of the subject such as the ankle. In some embodiments, the indicators may be overlaid with representations of a subject's body, such as the spine and head depicted in the figure, to aid in visualizing the location of detectors. In the depicted embodiment, the indicators 304 correspond to detectors located on the head are arranged in a typical EEG layout. However, other arrangements of the detectors and indicators are also contemplated including for example the use of text to either depict a particular state and/or readouts of actual measured values may be used in some embodiments.

In order to indicate the presence and concentration of a tracer detected by a particular detector, the indicators in the above described GUI may vary between two or more states. For example, in one embodiment, the indicators may vary between two or more colors, intensities, patterns, shapes, and/or sizes to indicate the presence or concentration of a tracer. Dynamic patterns and/or indicators may also be used such as pulsing indicators that change between two states to indicate information, growing bulleyes, growing spirals, etc. Text may be used in place of, or may be used in combination with the above noted states to provide additional information related to the detected tracer. In one such embodiment, an indicator may go from clear or black to yellow to indicate that system is on. The indicator may then transition from yellow to green to indicate that a tracer is present above a threshold concentration at the location of a particular detector. The indicator may then transition to a different shade or intensity of green, or any other appropriate color, to indicate that an effective amount of a therapeutic compound corresponding to a second threshold concentration of the tracer has been detected in the body portion. While a particular embodiment has been described above, it should be understood that any number of different ways of indicating the presence, concentration, and/or changes over time in the presence or concentration of a tracer within a particular body portion may be used as the disclosure is not so limited.

In addition to using a GUI interface, in some embodiments, it may be desirable to provide a visual indication of the presence, concentration, and/or changes over time in the presence or concentration of a tracer within a body portion that is observable by a subject wearing the detectors and/or persons near the subject. In one embodiment, a display, LED, or any other means of visually indicating the presence, concentration, and/or changes over time in the presence or concentration of a tracer is provided on a wearable structure. The indicators may be provided on any portion of a wearable structure including the detectors. However, in some cases the indicators may be located adjacent to, or on, the detectors. Therefore, as the one or more indicators transition from a first state indicating that no tracer has been detected above a first threshold concentration to at least a second state indicating a tracer has been detected above the threshold concentration, a person may observe either that a therapeutic compound has reached a target site and/or the person may view the progress of a therapeutic compound within a portion of the body as might be done for an intrathecal injection progressing along the spine and into the brain of a subject.

EXAMPLE

Wearable Vest Including Detectors Located Along the Spine

Figure 15:
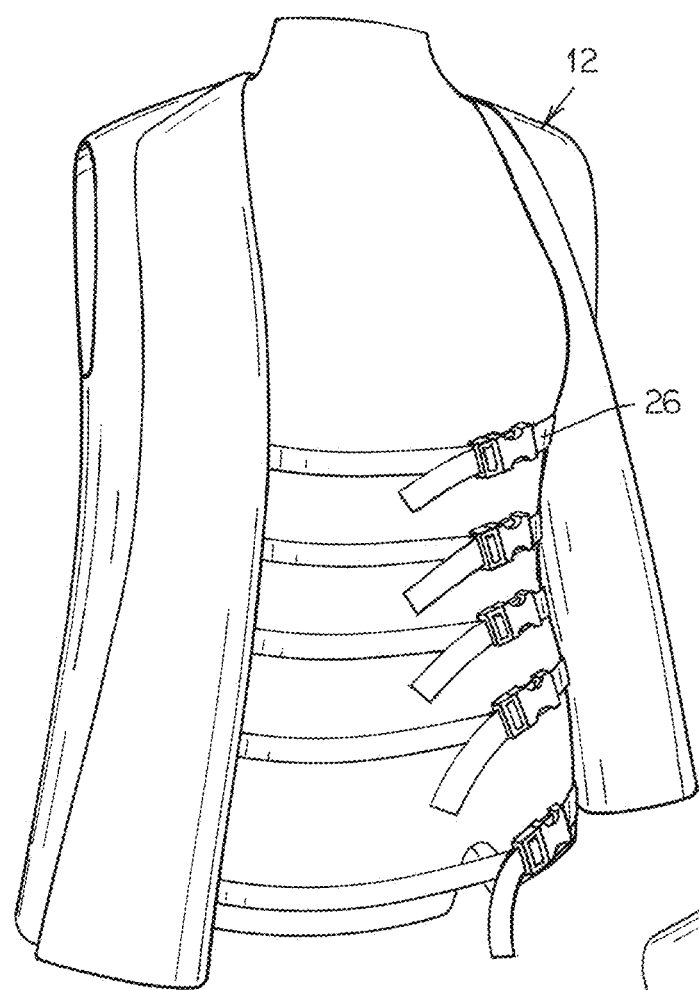
FIG. 15 is a photograph of the front of a vest including detectors along the spine and straps used for holding the detectors proximate the spine of a subject.
Figure 16:
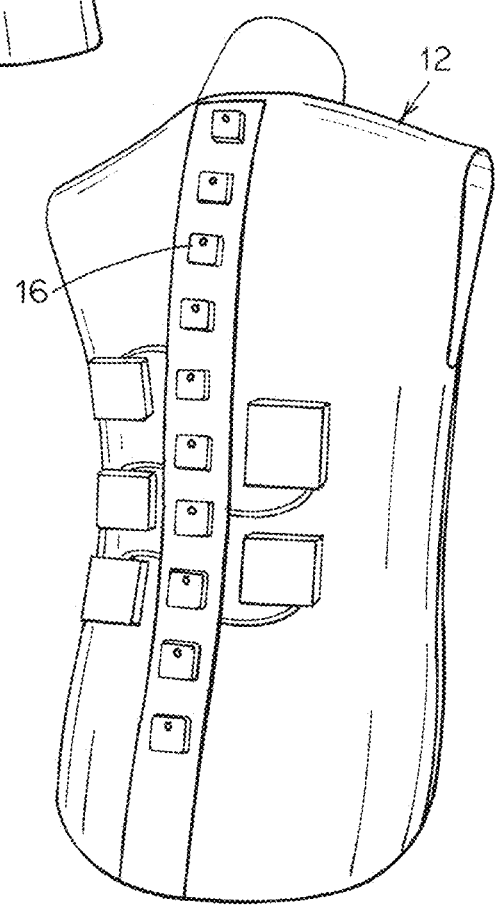
FIG. 16 is a photograph of the rear of a vest including detectors along the spine and straps used for holding the detectors proximate the spine of a subject.

FIGS. 15 and 16 present photographs of a wearable vest 12 having a plurality of detectors 14 extending along the spine of a subject when the vest is worn. The vest is made from a neoprene material and made to fit the entire torso. The detectors are CMOS cameras contained in outer plastic housings attached along the back of the vest so that they will extend along a spine of a person wear the vest. The vest also includes a series of straps 26 connected to a support running along the length of the detectors so that tightening the straps help maintain the detectors proximate the spine of a person wearing the vest as previously described.

EXAMPLE

Wearable Cap Including Detectors Distributed Around a Subject's Head

Figure 17:
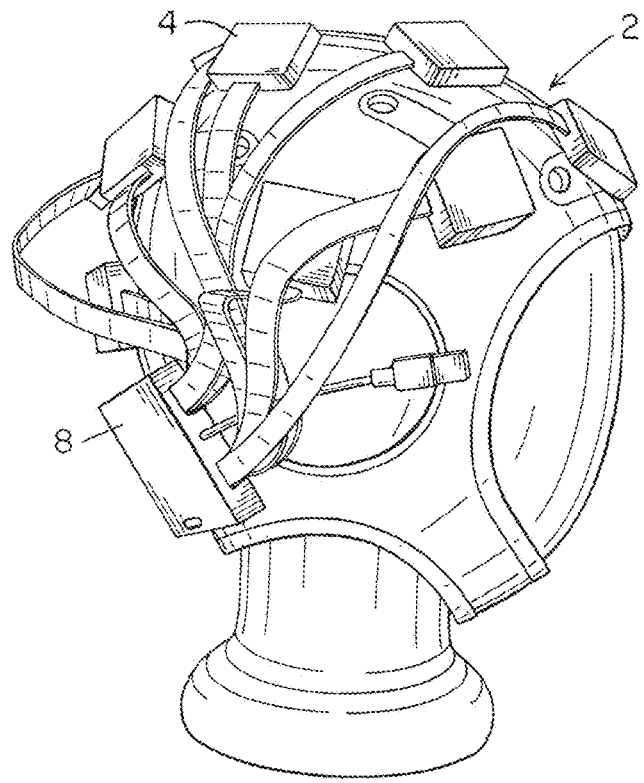
FIG. 17 is a photograph of the side of a cap including detectors distributed around the head of a subject.
Figure 18:
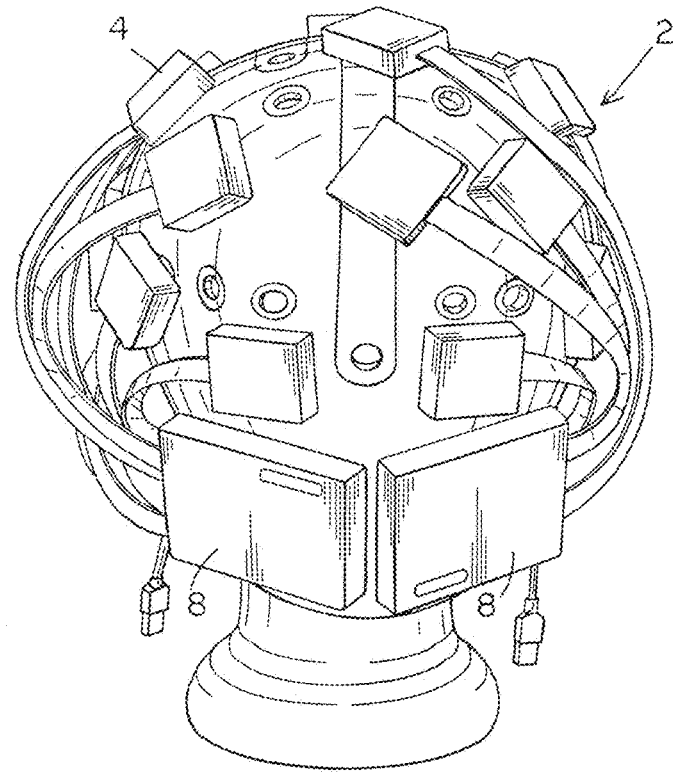
FIG. 18 is a photograph of the rear of a cap including detectors distributed around the head of a subject.

FIGS. 17 and 18 present photographs of a wearable cap 2 including a plurality of detectors 4 associated with the different hemispheres of the brain. The cap is a standard EEG layout cap made from neoprene. The detectors are CMOS cameras contained in outer plastic housings that include an interlocking feature positioned in the holes of the cap to position and attach the detectors to the cap. The detectors associated with the different hemispheres of the brain are connected to separate controllers 8 via the shown cables.

EXAMPLE

Wearable Detector for Monitoring an Extremity

Figure 19:
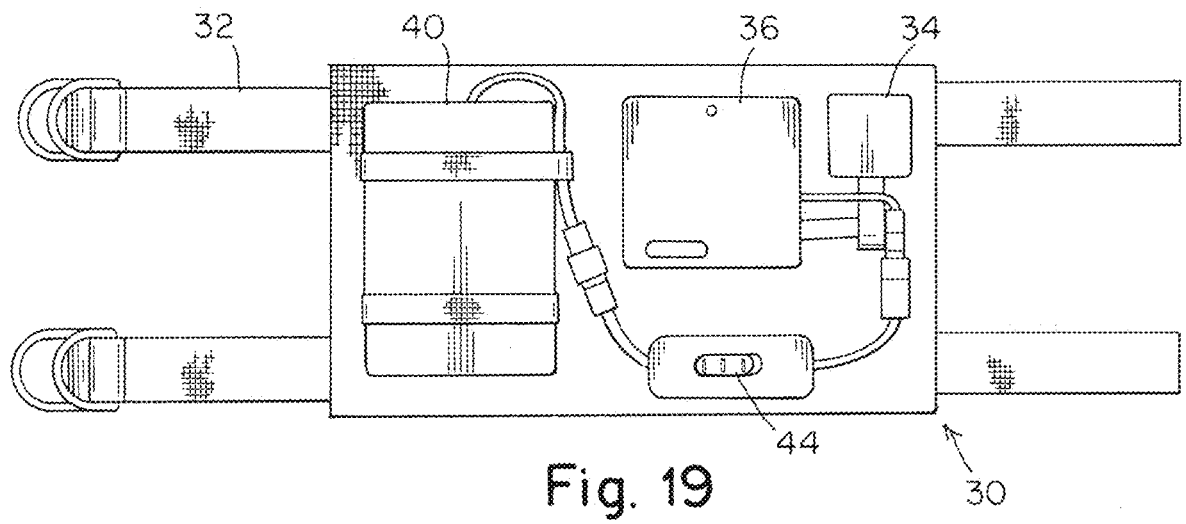
FIG. 19 is a photograph of an ankle bracelet including a detector.
Figure 20:
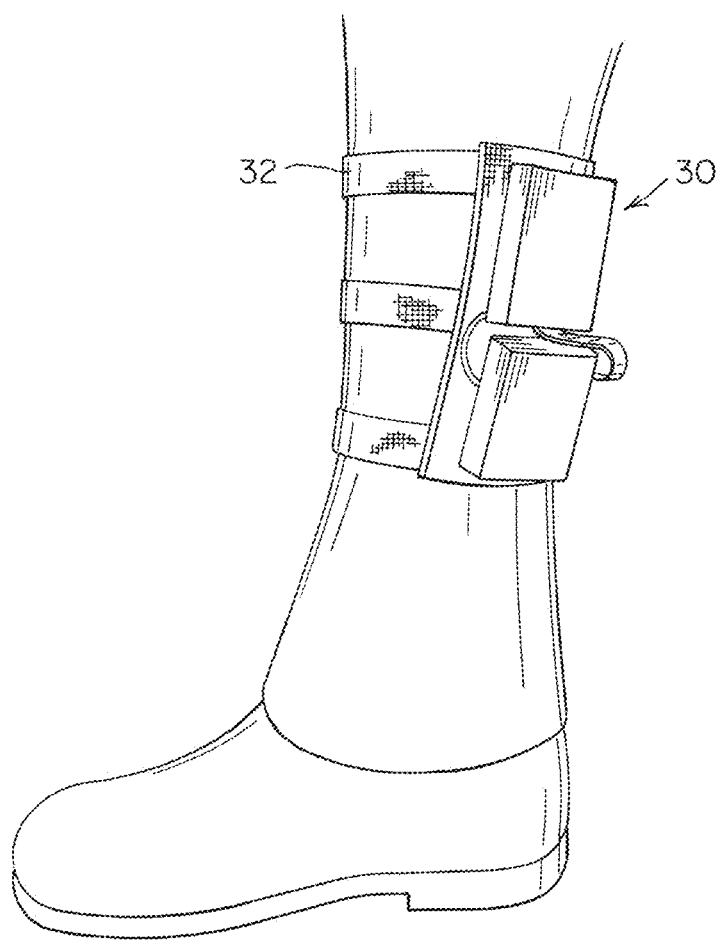
FIG. 20 is a photograph of an ankle bracelet including a detector positioned on the ankle of a subject.

FIGS. 19 and 20 are photographs of an ankle bracelet 30 that includes a detector 34 as well as an associated control 36, battery 40, and switch 44 positioned on a neoprene backing. The ankle bracelet is attached to the ankle of a subject via straps 32 which include simple D ring connectors for tightening on the subjects ankle as shown in FIG. 20.

EXAMPLE

Detection of Radioisotope Based Tracers Using a CMOS Chip

A CMOS chip located within a smartphone was used to monitor positrons emitted from a source with energies of 511 keV. As summarized in tables I and II below, CMOS chips found within a smartphone are able to detect a low-level source with a detection floor of about 0.3 uCi for just a single detector indicating this technique may be used for making drug pharmacokinetic measurements.

TABLE I

INTEGRATED DOSE RATES OF SMARTPHONE READINGS

| | Dose rate (mRem/hr) | |
|---|---|---|
| Sample | Device 13 | Device 15 |
| background | 0.017 +/− 0.006 | 0.012 +/− 0.005 |
| 1 | 2.02 +/− 0.06 | 1.58 +/− 0.06 |
| 2 | 0.53 +/− 0.03 | 0.30 +/− 0.03 |
| 3 | 0.11 +/− 0.01 | 0.12 +/− 0.02 |

TABLE II

ESTIMATED DETECTION LIMITS

| Integration time (hr) | Detection limit (μRem/hr) | Quantification limit (μRem/hr) | Approximate activity level at quantification limit (μCi) |
|---|---|---|---|
| 0.5 | 31 | 49 | 1.5 |
| 1 | 15 | 24 | 0.8 |
| 2 | 7.7 | 12 | 0.4 |
| 3 | 5.1 | 8 | 0.3 |

EXAMPLE

Invivo Testing Nonhuman Primate (NHP) Intrathecal Dosing

Figure 21:
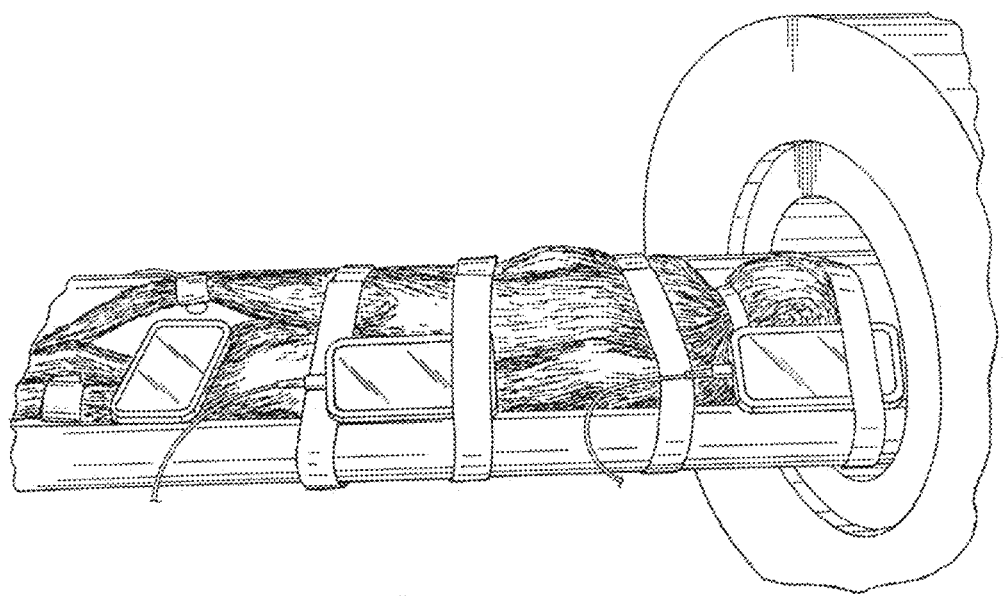
FIG. 21 is a photograph of cell phones placed along the body of a non-human primate intrathecally injected with a radioactive tracer.
Figure 22:
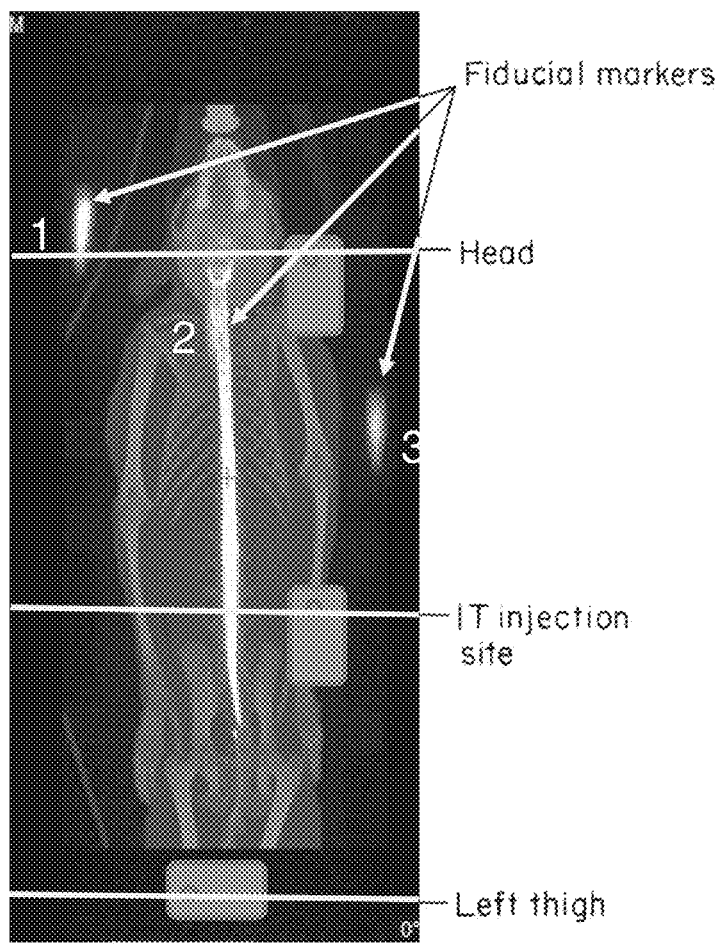
FIG. 22 is a schematic representation of the location of phone cameras overlaid with a PET image indicating the presence of a radiolabeled tracer within the intrathecal space and brain of a monkey.
Figure 23:
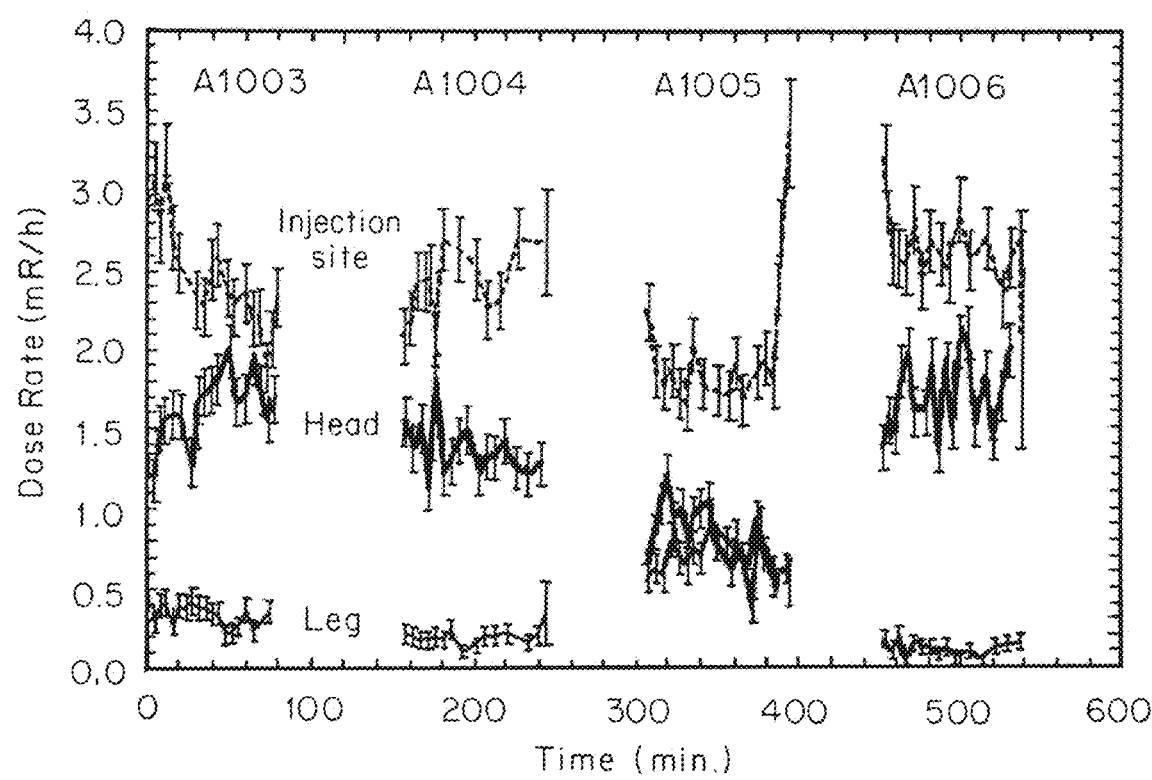
FIG. 23 is a graph of signals detected by a CMOS chip of radioactive tracers located at the positions along four separate non-human primates at the locations illustrated in FIGS. 22 and 23.

3 Samsung® galaxy mini phones including CMOS based cameras were modified using Gamma Pix software (Image Insight, Inc.). 3 hours of background data was collected prior to the intrathecal injection of $^{64}$Cu-DOTA into the NHP for radioactivity measurement studies. CMOS data collection as well as PET imaging were conducted at times ranging from 30 to 90 minutes post injection for 4 subjects A1003-A1006. FIGS. 21 and 22 show a photograph of the experimental setup and positioning of the smartphone cameras overlayed on a PET image of the $^{64}$Cu-DOTA within the NHP during the experiments. FIG. 23 presents the measured signals using the CMOS based cameras at the left thigh, intrathecal injection site, and head of the NHP subjects. As indicated by the graph the CMOS based cameras were capable of detecting the presence and changes in the signal associated with $^{64}$Cu-DOTA during the course of the experiments indicating that CMOS based detectors are capable of directly measuring a radiolabeled compound usable in medical applications.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A medical detector system comprising:
a wearable structure; and
a first detector that is coupled to the wearable structure such that the first detector is positioned proximate to a body portion of a subject when the wearable structure is worn by the subject, wherein the first detector includes a CMOS chip that directly detects a first radioactive tracer within the body portion of the subject.

2. The medical detector system of claim 1, wherein the wearable structure is wearable on the subject's head, and the body portion is the subject's brain.

3. The medical detector system of claim 1, wherein the wearable structure is wearable on the subject's torso, and the body portion is the subject's spine.

4. The medical detector system of claim 1, wherein the body portion is at least one of a thyroid, lymph node, salivary gland, eye, and deep vein.

5. The medical detector system of claim 1, wherein a housing of the first detector is opaque relative to at least emissions from the first radioactive tracer.

6. The medical detector system of claim 1, wherein the first detector detects at least the first radioactive tracer and a second radioactive tracer.

7. The medical detector system of claim 6, wherein the first detector discriminates between at least the first radioactive tracer and the second radioactive tracer.

8. A medical detector system comprising:
a structure sized and shaped to be positioned and held within a mouth of a subject; and
a first detector coupled to the structure and configured to detect at least a first radioactive tracer present within the brain of the subject when the structure is located in the mouth of the subject, wherein the first detector includes a housing that is radio opaque relative to at least radiation from the first radioactive tracer.

9. The medical detector system of claim 8, wherein the structure covers the soft palate and/or hard palate of the subject when positioned within the mouth of the subject.

10. The medical detector system of claim 8, wherein the housing includes at least one aperture directed towards the brain of the subject when the structure is positioned within the mouth of the subject.

11. The medical detector system of claim 8, wherein the first detector detects at least the first radioactive tracer and a second radioactive tracer.

12. The medical detector system of claim 11, wherein the first detector discriminates between at least the first radioactive tracer and the second radioactive tracer.

13. The medical detector system of claim 8, further comprising a processor configured to receive a signal from the first detector.

14. The medical detector system of claim 13, further comprising a wireless transmitter configural to transmit the signal from the first detector to the processor.

15. The medical detector system of claim 8, wherein the first detector is configured to detect a concentration of the first radioactive tracer within the brain of the subject.

16. The medical detector system of claim 15, wherein the first detector is configured to detect changes over time in the concentration of the first radioactive tracer within the brain of the subject.

17. The medical detector system of claim 1, further comprising a processor configured to receive a signal from the first detector.

18. The medical detector system of claim 17, further comprising a wireless transmitter configural to transmit the signal from the first detector to the processor.

19. The medical detector system of claim 1, wherein the first detector is configured to detect a concentration of the first radioactive tracer within the body portion of the subject.

20. The medical detector system of claim 19, wherein the first detector is configured to detect changes over time in the concentration of the first radioactive tracer within the body portion of the subject.

* * * * *